United States Patent [19]

Jones et al.

[11] Patent Number: 5,553,034

[45] Date of Patent: Sep. 3, 1996

[54] DIFFERENTIAL PRESSURE FLUID DENSITY INSTRUMENT

[75] Inventors: Stanley C. Jones, Littleton, Colo.; Daniel T. Georgi, Houston, Tex.

[73] Assignee: Western Atlas International, Inc., Houston, Tex.

[21] Appl. No.: 597,356

[22] Filed: Feb. 8, 1996

Related U.S. Application Data

[63] Continuation of Ser. No. 359,581, Dec. 20, 1994, abandoned.

[51] Int. Cl.$^6$ .................................................. E21B 49/10
[52] U.S. Cl. ............................ 367/25; 367/912; 175/48; 175/50; 73/152.05; 73/152.18
[58] Field of Search ........................ 367/25, 912; 175/48, 175/50; 166/250; 73/151, 152, 153

[56] References Cited

U.S. PATENT DOCUMENTS

| | | | |
|---|---|---|---|
| 3,616,688 | 11/1971 | Roussin et al. | 73/151 |
| 4,703,664 | 11/1987 | Kirkpatrick et al. | 73/866.5 |
| 4,805,449 | 2/1989 | Das | 73/151 |
| 4,860,580 | 8/1989 | Da Rocher | 73/155 |

*Primary Examiner*—J. Woodrow Eldred
*Attorney, Agent, or Firm*—Richard A. Fagin

[57] ABSTRACT

The present invention is a differential pressure fluid density production logging tool. The tool comprises an elongated housing adapted to traverse a wellbore. The housing has ports in hydraulic communication with the wellbore at spaced apart locations. The tool also comprises a differential pressure transducer having two inputs, a selective valve, and a reference tube filled with a liquid having a known density. The valve is selectively operable to shunt the inputs of the transducer, to connect the reference tube across the inputs of the transducer to calibrate the transducer, and to connect the ports across the inputs of the transducer to enable measurement of the fluids in the wellbore.

13 Claims, 3 Drawing Sheets

DIFFERENTIAL PRESSURE FLUID DENSITY INSTRUMENT

This is a continuation of application Ser. No. 08/359,581 filed on Dec. 20, 1994, now abandoned.

BACKGROUND OF THE INVENTION

1. Field of the Invention

The present invention is related to the field of electric wireline production logging tools. More specifically, the present invention is concerned with tools which measure the density of a fluid in a wellbore.

2. Discussion of the Relevant Art

Electric wireline production logging tools are used to determine volumes of various fluids entering a wellbore penetrating each formations, and the points of envy of the fluids within the wellbore. The fluids can include various quantities of gas, oil and water. By determining the points of entry and the volumes of the fluids entering the wellbore at each entry point, the wellbore operator may be able to take appropriate action in the event that fluids not desired to be produced from the wellbore appear in the total volume of produced fluid which reaches the earth's surface.

Various production logging instruments have been devised for determining fluid volume and points of fluid end, Production logging instruments include fluid density tools which measure the density of the fluid filling the wellbore. The fluid density tool typically transmits signals to the earth's surface over an armored electrical cable which correspond to the density of the fluid in the wellbore measured at a plurality of depths within the wellbore.

One type of fluid density tool enables determining the fluid density by measuring a differential pressure in the wellbore between at least two spaced apart locations along the tool. If the spaced apart locations are vertically separated, the differential pressure which exist between the spaced apart locations can be related to fluid density by the expression:

$$\rho = \frac{\Delta P}{g(\Delta h)} \qquad (1)$$

where $\rho$ is the fluid density; g is the local acceleration due to earth's gravity; $\Delta P$ is the differential pressure; and $\Delta h$ is the vertical separation between the spaced apart locations along the tool.

A differential pressure fluid density tool is known in the art. U.S. Pat. No. 3,616,688, issued to Bonnet et al, discloses an apparatus for determining fluid density by measuring differential fluid pressure between two spaced apart locations along the tool.

The differential pressure fluid density tool disclosed in the Bonnet patent has several drawbacks. Accurate measurement of differential pressure requires a differential pressure transducer which is sensitive to very small differences in pressure, on the order of 0.01 psi, applied across two pressure inputs to the transducer. Differential pressure transducers having this level of sensitivity are subject to destructive failure at relatively small values of differential pressure, on the order of 20 psi, applied across the transducer inputs. Destructive amounts of differential pressure can be encountered by the transducer for example, when the tool is inserted into the wellbore through a wellhead valve system attached to the top of the wellbore.

Another drawback to the differential pressure fluid density tool disclosed in the Bonnet patent is that the vertical separation between the spaced apart locations along the tool must be precisely known in order to determine the fluid density from the differential pressure measurement. Some wellbores are drilled directionally, and therefore have some inclination from vertical. If the tool is disposed in a non-vertical wellbore, the vertical separation between the spaced apart locations along the tool will not exactly correspond to the linear distance between the spaced apart locations. A measurement of the inclination from vertical, such as that provided by a directional survey, can be used to calculate mathematically the vertical separation between the spaced apart locations in a non-vertical wellbore, but directional surveys are frequently conducted at intervals as long as ninety feet within the wellbore. The actual inclination at some intervals of the wellbore may not be precisely determinable using a directional survey. Inaccuracy in determining inclination can cause inaccuracy in calculating the exact vertical separation between the spaced apart locations if the wellbore is highly deviated.

Another limitation of the fluid density tool disclosed in the Bonnet patent is that the differential pressure transducer is subject to variations in calibration when the transducer is exposed to different temperatures and absolute pressures. A typical wellbore has wide variations of pressure and temperature between the earth's surface and depths within the wellbore where the tool is used. In the tool disclosed in the Bonnet patent, the only calibration is to adjust the transducer output to indicate zero differential pressure with the tool lying flat, in air, at the earth's surface. The tool known in the art has no means for calibrating the transducer output to compensate for variations which may be induced by temperature and hydrostatic pressure.

It is an object of the present invention to provide a differential pressure fluid density tool which is selectively insensitive to differential pressure to protect the transducer from destructive failure.

It is a further object of the present invention to provide a differential pressure fluid density tool which makes differential pressure measurements which need not be corrected to account for inclination of the wellbore.

It is still a further object of the present invention to provide a differential pressure fluid density tool which has an internal means for compensating calibration changes in the differential pressure transducer measurement while the tool is disposed within the wellbore.

SUMMARY OF THE INVENTION

The present invention is a differential pressure fluid density production logging tool. The tool comprises an elongated housing adapted to traverse a wellbore. The housing has ports in hydraulic communication with the wellbore at spaced apart locations. The tool also comprises a differential pressure transducer having two inputs, a selective valve, and a reference tube filled with a liquid having a known density. The valve is selectively operable to shunt the inputs of the transducer, to connect the reference tube across the inputs of the transducer to calibrate the transducer, and to connect the ports across the inputs of the transducer to enable measurement of the fluids in the wellbore.

In a preferred embodiment of the invention, the valve comprises two, three-way valves each valve having a common port and two selective ports.

In an alternative embodiment of the invention, the selective valves of the first embodiment can be substituted by a single four-way valve.

DESCRIPTION OF THE PREFERRED EMBODIMENT

Figure 1:
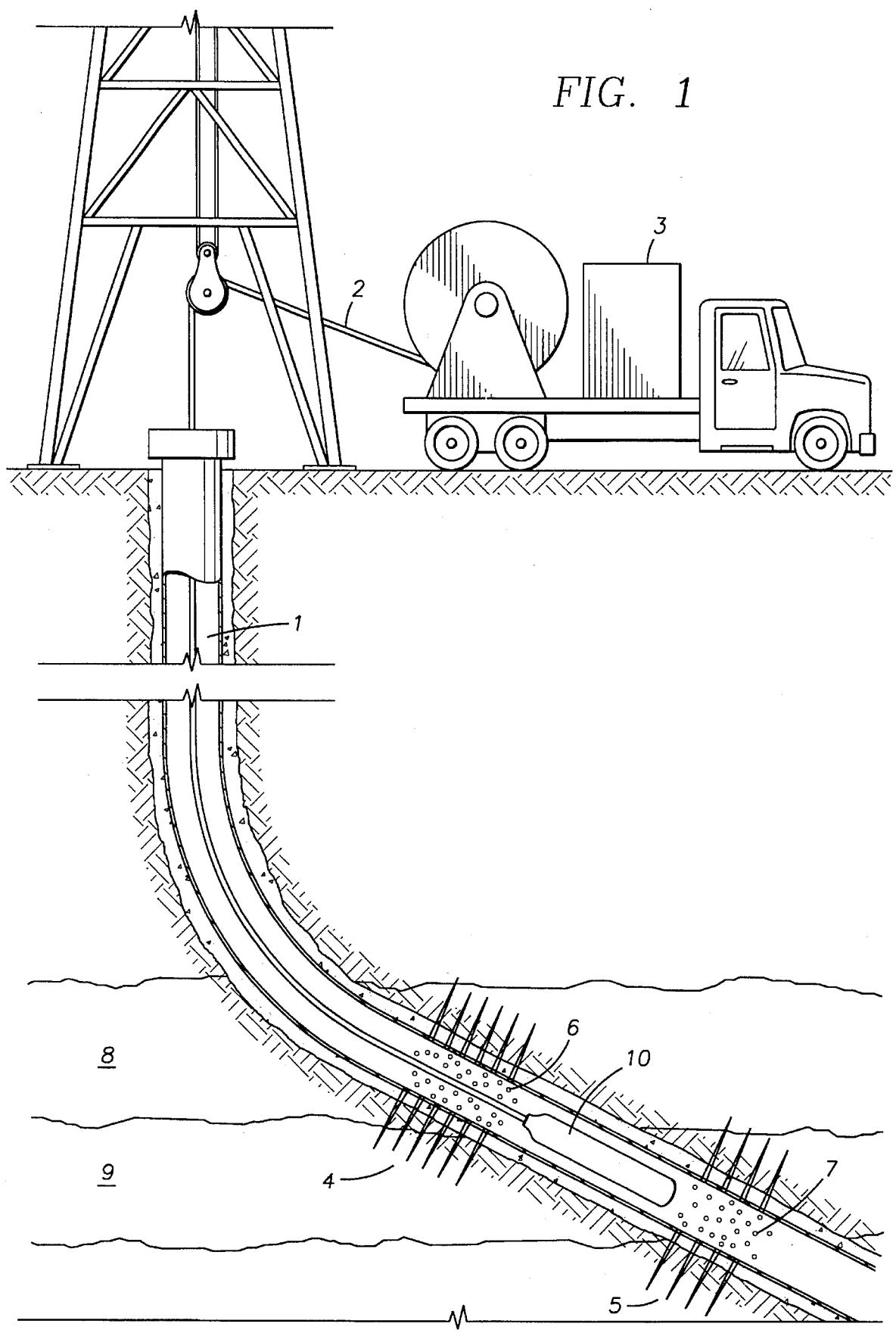
FIG. 1 shows the invention lowered into a wellbore by a wireline.

Operation of the present invention in a wellbore can be better understood by referring to FIG. 1. An electric wireline or cable 2 comprising at least one insulated electrical conductor (not shown) is typically lowered into a wellbore 1 by means of a surface logging unit 3. A logging tool 10 comprising the fluid density instrument of the present invention is attached to an end of the cable 2 which is lowered into the wellbore 1. The logging unit 3 also comprises equipment (not shown separately) for sending electrical power to the tool 10, and receiving and interpreting signals transmitted up the cable 2 by the tool 10.

A first zone 4 completed in an upper earth formation 8, and a second zone 5 completed in a lower earth formation 9 each provide hydraulic communication into the wellbore 1, enabling a first fluid 6 contained in the upper earth formation 8 and a second fluid 7, which may be of a different density than the first fluid 6, contained in the lower earth formation 9 to flow into the wellbore 1. As the tool 10 is moved past the zones 4, 5 the tool 10 makes measurements corresponding to the relative volumes of the first 6 and second 7 fluids entering the wellbore 1 from the upper 8 and lower 9 earth formations, respectively.

Figure 2:
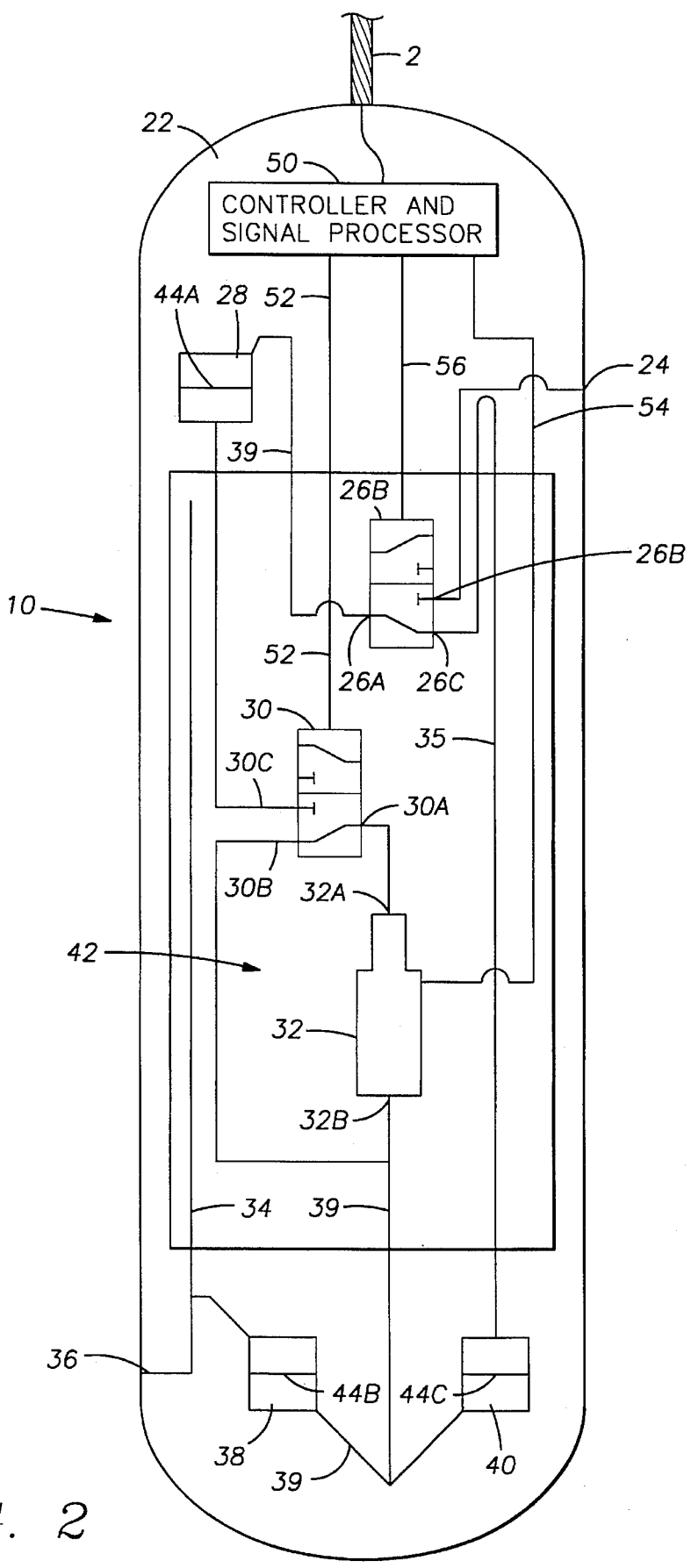
FIG. 2 shows the mechanical configuration of the invention.

FIG. 2 shows the tool 10 of FIG. 1 in more detail. A housing 22 is attached at one end to the cable 2, and contains the operating components of the tool 10. The housing 22 also provides spaced apart locations for an upper port 24 and a lower port 36, which can be machined through a wall of the housing 22. The housing 22 also defines an inner chamber 42 which traverses substantially the entire distance between the upper port 24 and the lower port 36, and is filled with a substantially incompressible fluid, which in the present embodiment can be silicone oil. The inner chamber 42, when filled with silicone oil, provides hydrostatic pressure balancing to the housing 22, which enables the housing 22 to be constructed without requiring the strength to resist external hydrostatic pressure generated by the fluids 6, 7 present in the wellbore 1.

The tool 10 can include a controller and signal processor 50, disposed within the housing 22 and electrically connected to the conductor (not shown) forming part of the cable 2. The controller 50 imparts signals to the cable 2 corresponding to the output of a differential pressure transducer 32 disposed in the housing 22. The transducer 32 is connected to the controller 50 by an electrical signal line 54. The signals from the tool 10 can be transmitted to the surface unit 3, or alternatively the transducer 32 output can be recorded in the controller 50.

The controller 50 also decodes command and operating signals sent from the surface unit 3 upon control of the operator, to actuate first 30 and second 26 electrically actuated solenoid valves disposed within the chamber 42 and connected to the controller 50 by electrical control lines 52 and 56, respectively. The valves 30, 26 are disposed within the chamber 42, which enables hydrostatic pressure in the chamber 42 to substantially balance internal and external pressures in the valves 30, 26. The valves 30, 26 therefore can be constructed without the ability to contain high pressures.

The upper port 24 and the lower port 36 are in hydraulic communication with the fluids (shown as 6, 7 in FIG. 1) in the wellbore 1 at spaced apart locations. A differential pressure can be present between the ports 24, 36 which is related to the density of the combined fluids 6, 7 in the wellbore 1 as previously described in equation 1. The distance between the ports 24, 36 in the present embodiment typically can be 3 feet. It is contemplated that the ports 24, 36 can be spaced at a greater or lesser distance depending on, for example, the expected type of fluids 6, 7 filling the wellbore 1, the inclination of the wellbore 1 from vertical, and the required resolution of the differential pressure measurement, since greater distance between the upper 24 and lower 36 port will increase the magnitude of the differential pressure between the ports 24, 36 if all other conditions remain constant.

The lower port 36 is also in hydraulic communication with one end of a first lower expansion well 38 located inside the housing 22. The first lower well 38 substantially prevents the fluids 6, 7 in the wellbore 1 present at the lower port 36 from entering hydraulic signal lines 39 connected to the other end of the well 38. The signal lines 39 can be filled with silicone oil such as the oil filling the chamber 42, or a similar fluid having a known density. The signal lines in the present embodiment can comprise steel tubing having an inside diameter of $\frac{1}{32}$ inch. As will be further explained, the density of the silicone oil filling the lines 39 should be precisely known at any temperature and pressure to which the tool 10 may be subjected while operated in the wellbore 1.

The lower port 36 is also hydraulically connected to the lower end of a standpipe 34 which can be filled with silicone oil. The silicone oil used in the standpipe 34 can be the same type of oil used to fill the signal lines 39 and the chamber 42. At its upper end the standpipe 34 is in hydraulic communication with the chamber 42. The standpipe 34 extends substantially to the top of the inner chamber 42. In the event some of the fluids 6, 7 in the wellbore enter the chamber 42 through the standpipe 34, the fluids 6, 7 will tend to remain in the upper part of the chamber 42 since the fluids 6, 7 will typically be less dense than the silicone oil. The fluids 6, 7 will generally be discharged back into the wellbore 1 as the silicone oil in the chamber 42 expands due to temperature increase or decompression.

Incremental changes in the total volume of the silicone oil contained in the lines 39 and the well 38 are possible as the tool 10 is exposed to different temperatures and pressures in the wellbore 1, since the silicone oil is likely to undergo various degrees of thermal expansion and hydrostatic compression as the tool 10 is lowered into the wellbore 1. It is necessary to maintain nearly constant fluid level in the signal lines to accurately determine density differences between the silicone oil and the fluids 6, 7 in the wellbore 1 as will be further explained. The diameter of the signal lines 39 is small relative to the radius of the well 38. In the present embodiment the well 38 can have a diameter of ¼ inch. The length of the well 38 in the present embodiment can be about ½ inch. Because the diameter of the well 38 is about eight times that of the lines 39, the cross-sectional area of the well 38 is about 64 times that of the lines 39. If an interface between the silicone oil and a different fluid, such as the fluids 6, 7 in the wellbore 1, is maintained in the well 38, incremental changes in volume of the silicone oil contained in the well 38 and the lines 39 will result in only very small changes in overall length of the oil column in the lines 39 and the well 38 due to the relatively large cross-sectional area of the well 38.

The first lower well 38 can also be equipped with a separator cup 44B made of a polymeric material such as phenylene polysulfide, sold under the trade name RYTON. The cup 44B is typically disposed at the interface between the silicone oil and the other fluids 6, 7, and substantially prevents mixing of the fluids 6,7 in the wellbore 1 with the silicone oil in the signal lines 39.

The signal lines 39 also are hydraulically connected to a first input 32B of the transducer 32 and to one end of a second well 40, similar in construction and purpose to the first well 38. The second well 40 can also be equipped with a cup 44C similar to the cup 44B disposed in the first well 38. At the other end the second well 40 is hydraulically connected to a lower end of a reference tube 35 disposed in the housing 22, the tube 35 extending substantially the entire distance between the lower port 36 and the upper port 24. The reference tube 35 is filled with a liquid having a known density different from the density of the silicone oil. The density of the liquid should also be known at a range of pressures and temperatures corresponding to the range of pressures and temperatures expected to be encountered in the wellbore 1 by the tool 10, and the density should be sufficiently different than the density of the silicone oil filling the signal lines 39, so that a differential pressure developed by the fluid between top and bottom of the reference tube 35, and developed by the silicone oil filling the lines 39, will be within the resolution of the transducer 32, as will be further explained. In the present embodiment the requirements for the liquid in the reference tube 35 can be fulfilled by dodecane.

A second input 32A of the transducer 32 is connected to a common port 30A of the first valve 30. The valve 30 in the present embodiment can be an electrically actuated solenoid three-way valve. The first valve 30 is actuated by the controller 50 when the controller 50 decodes a command from the surface unit 3. The command can be entered in the surface unit 3 by the operator. A first selective port 30B of the first valve 30 is connected to the signal lines 39 and the first input 32B of the transducer 32.

When the first valve 30 is connects the common 30A to the first selective port 30B, the transducer 32 becomes hydraulically shunted. When the transducer 32 is shunted, high differential pressure between the upper port 24 and the lower port 36 such as that which can occur when inserting the tool 10 into the wellbore 1, is prevented from reaching the transducer 32. Shunting can prevent damage to the transducer 32 by preventing application of high differential pressure to the transducer 32.

The differential pressure applied to the transducer 32 is substantially equal to zero when the first valve 30 is selected to shunt the transducer 32. A signal output of the transducer 32 at zero differential pressure, known as offset, which may be caused to change by temperature or hydrostatic pressure, can be measured when the first valve 30 is selected to shunt the transducer 32. The offset thus measured can be calibrated out of subsequent measurement of differential pressure generated by the fluids 6, 7 in the wellbore 1 as will be further explained.

A second selective port 30C of the first valve 30 is connected to one end of a third well 28 similar in construction and purpose to the first well 38. The third well 28 can be equipped with a cup 44A similar to the other cups 44B, 44C. The other end of the third well 28 is hydraulically connected to a common port 26A of the second valve 26.

The second valve 26 in the present embodiment can be a solenoid energized three-way valve actuated by the controller 50 upon decoding a command from the surface unit 3, substantially the same as the first valve 30. The second valve 26 has a first selective port 26B connected to the upper port 24, and a second selective port 26C connected to the upper end of the reference tube 35.

When the first valve 30 is operated to selectively connect its common port 30A to the third well 28, and the second valve 26 is operated to make hydraulic connection to the upper port 24, the transducer 32 is hydraulically connected at the second input 32A to the upper port 24 and the first input 32B of the transducer 32 is connected to the lower port 36, enabling a measurement to be made corresponding to the differential pressure generated by the fluids 6,7 in the wellbore 1.

Because the signal lines 39 are filled with silicone oil, the differential pressure actually developed across the transducer 32 will be related to: a static differential pressure generated by the silicone oil in the signal lines 39 corresponding to the density of the silicone oil and the height of the silicone oil column in the lines 39 between the cup 44A in the second well 28 and the cup 44B in the first well 38; and the differential pressure caused by the fluids 6, 7 in the wellbore 1 between the upper port 24 and the lower port 36.

As previously explained, the overall length of the column of the silicone oil in the lines 39 is maintained substantially constant even though the silicone oil may be slightly compressed or expanded when the tool 10 is inserted into the wellbore 1, because the wells 38, 40, 28 have a large diameter relative to the diameter of the lines 39. Therefore, small changes in the silicone oil volume will not materially affect the overall length of the silicone oil column, which maintains consistency of the differential pressure measurement made by the transducer 32 relative to the wellbore 1.

When the second valve 26 is selected to connect the second input 32A of the transducer 32 to the upper end of the reference tube 35, the differential pressure across the transducer 32 is related only to the difference in density between the silicone oil and the dodecane reference fluid, and to the effective vertical height of the columns of reference fluid and silicone oil. Because both the silicone oil and the reference fluid densities are known, and the overall lengths of the columns of silicone oil and dodecane in the reference tube 35 are also known, the differential pressure measurement thus made can directly calibrate the effects of inclination of the tool 10 from vertical, effectively eliminating the need to separately measure the inclination of the tool 10 from vertical.

The measurement made when the second valve 26 is selected to connect the second input 32A of the transducer 32 to the upper end of the reference tube 35, can also be used to calibrate changes in the gain of the transducer 32 which may be caused by external hydrostatic pressure and temperature on the transducer 32, because the differential pressure signal generated by the transducer 32 is eventually scaled into a measurement of density. Since the densities of the dodecane in the reference tube 35 and the silicone oil in the lines 39 are known, the transducer 32 signal can be directly scaled into a measurement corresponding to the difference in the two known densities. The gain of the transducer 32 is defined as the ratio of the magnitude of an output signal generated by the transducer 32 in response to a particular magnitude differential pressure applied across the inputs 32A, 32B of the transducer 32.

In actual use in the wellbore 1, the tool 10 will be initially operated with the first valve 30 selected to shunt the transducer, and the tool positioned in the wellbore 1 near the upper zone 4 and the lower zone 5 to obtain a first measurement which can be used for offset calibration. Next, the tool will be operated having the first valve 30 set to connect the transducer 32 to select the second valve 26, and the second valve set to select the reference tube 35. The tool will again be positioned next to the upper zone 4 and the lower zone 5 to obtain a second measurement which is a calibration of the transducer 32 gain and the tool 10 inclination. Finally the tool 10 will be operated with the second valve 26 set to select the upper port 24, and the tool positioned next to the zones 4, 5 to obtain third measurements corresponding to the fluids 6, 7 in the wellbore. The first, second and third measurements can be combined in the surface unit 3 to calculate calibrated fluid density measurements.

It is contemplated that the first, second and third measurements can be performed successively at time intervals of ⅛ second to several seconds duration, by appropriately programming the controller 50 to operate the valves 30, 26 automatically, so that while the tool 10 is moved by the upper 4 and lower 5 zones, the combined measurement can be calculated using data obtained during only one run of the tool 10 by the zones 4, 5.

DESCRIPTION OF AN ALTERNATIVE EMBODIMENT

Figure 3:
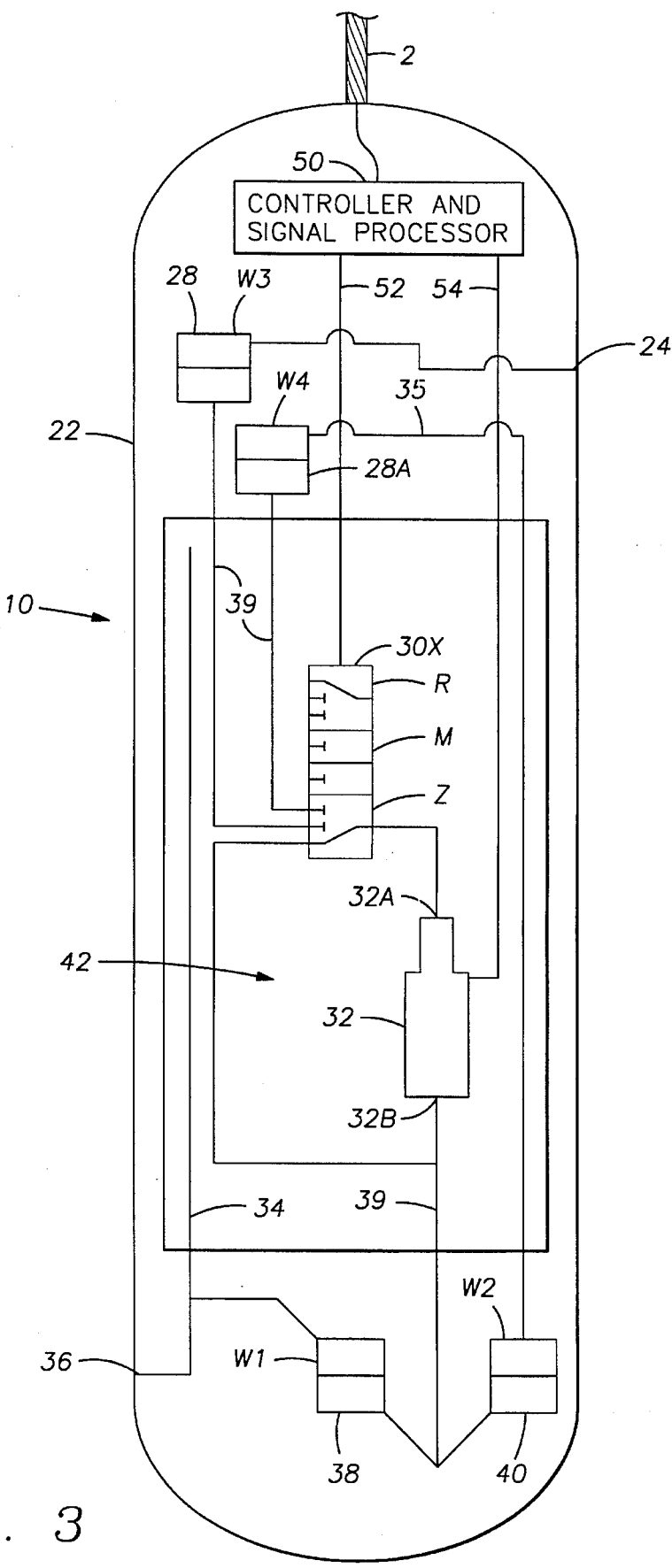
FIG. 3 shows an alternative selective valve arrangement.

Alternative means for selective hydraulic connection of the transducer 32 can accomplish the same offset and calibration measurements as the valves disclosed in the first embodiment. As shown in FIG. 3, a single electrically actuated solenoid valve 30X having three selective ports M, Z, and R can selectively connect the transducer 32 to the reference tube 35, the upper port 24, or shunt the transducer by selecting the Z port. The valve 30X in the alternative embodiment can be connected to the controller 50 and actuated by control from the operator as in the first embodiment.

The scope of the invention should be limited only by the claims appended hereto.

What is claimed is:

1. A production logging tool for determining density of a fluid in a wellbore penetrating an earth formation by measuring a differential pressure between spaced apart locations along said tool, said tool comprising:

an elongated housing adapted to traverse said wellbore, said housing having two ports at spaced apart locations along said housing, said ports in hydraulic communication with said wellbore;

a differential pressure transducer disposed within said housing, said transducer having two pressure inputs;

a reference tube disposed within said housing, said reference tube having two ends, said reference tube filled with a liquid of known density; and a valve, interconnected to said transducer, said valve selectively operable to hydraulically connect together said two inputs of said transducer to shunt said transducer, said valve selectively operable to hydraulically connect said reference tube across said inputs of said transducer to calibrate said transducer, said valve selectively operable to connect said ports across said inputs of said transducer to enable measurement of said fluid in said wellbore.

2. The apparatus as defined in claim 1 wherein said liquid of known density comprises dodecane.

3. The apparatus as defined in claim 1 further comprising a first expansion well hydraulically interposed between one of said ports and one of said inputs of said transducer, and a second expansion well hydraulically interposed between said other port and said other input of said transducer, said expansion wells at least partially filled with a substantially incompressible fluid.

4. The apparatus as defined in claim 3 wherein said first expansion well and said second expansion well further comprise a sealing cup consisting essentially of a polymeric material.

5. The apparatus as defined in claim 1 wherein said valve comprises:

a first three-way valve having a common port connected to said one input of said transducer, a first selective port, a second selective port connected to said other input to said transducer; and a second three-way valve having a common port connected to said first selective port of said first three-way valve, a first selective port connected to said other port in said housing, and a second selective port connected to one end of said reference tube.

6. A production logging tool for determining density of a fluid in a wellbore penetrating an earth formation by measuring a differential pressure between spaced apart locations along the tool, said tool comprising:

an elongated housing adapted to traverse said wellbore, said housing having ports at spaced apart locations along said housing, said ports in hydraulic communication with said wellbore;

a differential pressure transducer disposed within said housing, said transducer having two pressure inputs; and a valve disposed within said housing and interconnected to said transducer to and selectively operable to hydraulically connect together said inputs of said transducer to shunt said transducer, said valve selectively operable to connect said ports across said inputs of said transducer to make measurements of said fluid in said wellbore.

7. The apparatus as defined in claim 6 wherein said selective valve comprises a three-way valve having a common port connected to one input of said transducer, a first selective port hydraulically connected to one of said ports in said housing, and a second selective port connected to the other input of said transducer.

8. A method of protecting a differential pressure transducer forming part of a differential pressure fluid density logging tool, said transducer having a first and second input, said tool having a housing including ports at spaced apart locations along said tool, said first input of said transducer in hydraulic communication with one of said ports, said method comprising the steps of:

operating a selective valve in said tool to shunt said first input and said second input; and operating said selective valve to put said second input of said transducer in hydraulic communication with another port in said tool.

9. A production logging tool for determining density of a fluid in a wellbore by measuring a differential pressure between spaced apart locations along said tool, comprising:

an elongated housing having ports at spaced apart locations thereon, said ports in hydraulic communication with said wellbore;

a differential pressure transducer disposed within said housing, said transducer having two pressure inputs;

a reference tube disposed within said tool, said reference tube having two ends, said reference tube filled with a liquid of known density; and a selective valve interconnected with said transducer, said valve selectively operable to hydraulically connect said reference tube across said inputs of said transducer to calibrate said transducer, said valve selectively operable to connect said ports across said inputs to said transducer to enable measurement of said fluid in said wellbore.

10. The apparatus as defined in claim 9 wherein said selective valve comprises a three-way valve having a common port connected to one input of said transducer, a first selective port hydraulically connected to one of said ports in said housing, and a second selective port connected to one end of said reference tube.

11. The apparatus as defined in claim 9 wherein said fluid having a known density comprises dodecane.

12. A method of calibrating a measurement of differential pressure corresponding to density of a fluid in a wellbore using a tool having a differential pressure transducer for making measurements corresponding to the differential pressure generated by said fluid in said wellbore at spaced apart locations along said tool, said method comprising the steps of:

lowering said tool into said wellbore;

positioning said tool by an interval of interest in said wellbore;

operating a selective valve in said tool to put said transducer in hydraulic communication with a reference tube disposed within said tool, said reference tube filled with a fluid having a known density;

positioning said tool by said interval of interest so that a calibrate signal from said transducer is generated;

operating said selective valve to put said transducer in hydraulic communication with said wellbore at said spaced apart locations along said tool;

positioning said tool by said interval of interest so that a measure signal corresponding to said fluid in said wellbore is generated; and calculating a corrected differential pressure measurement by combining said calibrate signal and said measure signal.

13. The method as defined in claim 12 wherein said fluid having a known density comprises dodecane.

* * * * *